United States Patent [19]

Desjonqueres

[11] Patent Number: 5,254,585
[45] Date of Patent: Oct. 19, 1993

[54] USE OF PEROXIDIZED LIPIDS FOR THE PREPARATION OF A DRUG INTENDED FOR THE TREATMENT OF CIRCULATORY INSUFFICIENCIES BY LOCAL APPLICATION

[75] Inventor: Stéphane Desjonqueres, Montesson, France

[73] Assignee: Laboratoires Carilene, Montesson, France

[21] Appl. No.: 784,397
[22] PCT Filed: Jul. 2, 1990
[86] PCT No.: PCT/FR90/00494
 § 371 Date: Dec. 30, 1991
 § 102(e) Date: Dec. 30, 1991
[87] PCT Pub. No.: WO91/00101
 PCT Pub. Date: Jan. 10, 1991

[30] Foreign Application Priority Data
 Jul. 3, 1989 [FR] France .................. 89 08883

[51] Int. Cl.$^5$ ............................................. A61K 31/23
[52] U.S. Cl. ........................... 514/552; 424/195.1; 514/824
[58] Field of Search ............... 424/195.1; 514/552

[56] References Cited

FOREIGN PATENT DOCUMENTS

| | | |
|---|---|---|
| 117962 | 9/1984 | European Pat. Off. . |
| 225831 | 6/1987 | European Pat. Off. . |
| 225832 | 6/1987 | European Pat. Off. . |
| 225833 | 6/1987 | European Pat. Off. . |
| 226506 | 6/1987 | European Pat. Off. . |
| 239535 | 12/1988 | European Pat. Off. . |
| 2330 | 12/1962 | France . |
| 2539142 | 7/1984 | France . |
| 2591112 | 6/1987 | France . |

*Primary Examiner*—John W. Rollins
*Attorney, Agent, or Firm*—Dennison, Meserole, Pollack & Scheiner

[57] ABSTRACT

The present invention relates to the use of peroxidized lipids, having a degree of peroxidation of between 50 and 200 milliequivalents per kilogram, preferably of between 50 and 150 milliequivalents per kilogram, for the preparation of a pharmaceutical composition intended for the treatment of circulatory insufficiencies, and in particular male sexual asthenia, by local application.

25 Claims, No Drawings

USE OF PEROXIDIZED LIPIDS FOR THE PREPARATION OF A DRUG INTENDED FOR THE TREATMENT OF CIRCULATORY INSUFFICIENCIES BY LOCAL APPLICATION

The present invention relates in general terms to a novel therapeutic indication for known products and relates essentially to the use of peroxidized lipids for the preparation of a drug intended for the treatment of circulatory insufficiencies, and especially male sexual asthenia, by local application.

It is known that many people suffer from circulatory insufficiency of arterial or venous origin, which is often chronic.

Circulatory insufficiencies are sometimes of a local and benign nature, manifesting themselves for example by a feeling of painful numbness at the finger ends caused by severe cold (tingling), or else of heaviness in the lower limbs.

Circulatory insufficiencies can also manifest themselves in much more serious forms associated with an arrest of the blood circulation (ischemia), which is capable of causing localized necrosis. Arterial or venous leg ulcers, for example, are the result of such a circulatory insufficiency and are a clinical manifestation of insufficient irrigation of the superficial and deep tissues by the blood flow.

Numerous treatments have hitherto been proposed for overcoming these insufficiencies.

Thus it has already been recommended to use numerous vasodilative or vasoprotective products by oral or percutaneous administration, often by perfusion.

However, these products have many undesirable side-effects, so their use is restricted to the most serious cases of circulatory insufficiency.

Moreover, tissue revascularization products have so far never been proposed which are totally devoid of toxicity and capable of being applied locally and whose use could be envisaged for the treatment of circulatory insufficiency at all stages.

It has been discovered that certain peroxidized lipids have a very great efficacy in tissue revascularization when applied locally, and that these products do not cause any undesirable side-effects; it is this discovery which forms the basis of the present invention.

Thus the present invention relates to the use of peroxidized lipids, having a degree of peroxidation of between 50 and 200 milliequivalents per kilogram, preferably of between 50 and 150 milliequivalents per kilogram, for the preparation of a pharmaceutical composition intended for the treatment of circulatory insufficiencies, and in particular male sexual asthenia, by local application.

It was observed that a significant efficacy was not obtained with a degree of peroxidation of less than 50 milliequivalents per kilogram.

Furthermore, detrimental free radicals were generated with a degree of peroxidation of more than 200 milliequivalents per kilogram.

The peroxidized lipids used according to the invention are known products prepared from lipids, for example by saturation with oxygen and intense and controlled exposure to ultraviolet rays.

These products have been described especially in the following documents: BSM No. 2330 M; EP-A-293 535; FR-A-2 591 112; EP-A-225 831; EP-A-225 832; EP-A-225 833; EP-A-226 506; FR-A-2 461 744; FR-A-2 539 142 and EP-A-117 962.

In these documents of the prior art, these compounds are presented as being capable of use in the treatment of certain complaints, especially in rheumatology or traumatology, or else as cicatrizing products.

However, the teaching of this state of the art contained neither an indication nor even a remote suggestion of the use of these products for the preparation of a pharmaceutical composition intended for the treatment of circulatory insufficiencies.

It has been found, totally surprisingly and unexpectedly, that the local application of these products is capable of increasing, to a remarkable extent, not only the superficial blood flow but also the subcutaneous or deep blood flow. In particular, it has been found that these products cause a doubling of the blood flow compared with that prior to the application of the product. This increase in blood flow is substantially greater than that obtained with conventional vasodilative products employed in perfusion, and appears to be the result of a different mechanism of action.

The peroxidized lipids capable of being used according to the invention can have a very varied chemical nature, but must necessarily have a degree of peroxidation, measured by the AFNOR method, of between 50 and 200 milliequivalents per kilogram and preferably of between 50 and 150 milliequivalents per kilogram.

In one particular embodiment, these lipids advantageously have a content of oxidized glycerides of between 5 and 40%.

According to the invention, the peroxidized lipid used is preferably at least one peroxide obtained by the peroxidation of lipids of vegetable origin, for example in the form of at least one natural vegetable oil. These oils are preferably selected among sweet-almond oil, hazelnut oil, peanut oil, maize oil, grapeseed oil, sesame oil and safflower oil.

In one particular embodiment of the invention, the peroxidized lipids used consist mainly or predominantly of triglycerides of the general formula

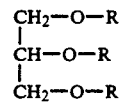

in which the radicals R are represented predominantly by octadecanoic and peroxidized octadecanoic acids.

According to one particular characteristic of the invention, these products are used for the preparation of a pharmaceutical composition intended for local application, and are generally in the form of a cream or a gel. It is also possible to envisage compositions in the form of a liquid or else in the form of soft capsules containing the peroxidized lipids.

Expressed in percentages by weight, a pharmaceutical composition prepared in this way comprises 2 to 99% of peroxidized lipids and about 1% of fragrance, as well as pharmaceutically acceptable excipients and demineralized water.

Advantageously, this pharmaceutical composition is in the form of a cream containing:

| | |
|---|---|
| cetyl alcohol | 2.0% |
| stearic acid | 5.0% |
| peroxidized lipids | 25.0% |

| -continued | |
|---|---|
| silicones | 0.5% |
| propylene glycol | 3.0% |
| triethanolamine | 0.2% |
| fragrance | 0.8% |
| non-ionic emulsifier | 6.0% |
| antimicrobial agent | 0.3% |
| demineralized water q.s.p. | 100 |

The blood flow-increasing effect of the compounds used according to the invention was determined experimentally from Doppler measurements of the circulation rate in superficial vessels and measurements of the overall superficial and deep circulation by rheoplethysmography.

The following Examples will provide an illustration of the present invention.

EXAMPLE 1

Preparation of a pharmaceutical composition based on peroxidized lipids originating from a commercially available virgin safflower oil Commercially available virgin safflower oil having the following principal characteristics:

| peroxide number | 18.70 meq/kg |
|---|---|
| oxidized glyceride | 4.18% |
| viscosity at 50° C. | 23.2 centistokes | is subjected to a peroxidation treatment as described in the document FR-A-2 461 744.

This method consists in storing the safflower oil in a stainless steel vat. This vat is covered with a hinged hood capable of collecting the vapors and acting as a support for an ultraviolet radiation lamp, for example a PHILIPS type HP 4 of 125 W.

This vat is fed continuously by an air pump, for example at a rate of 30 l/minute, to produce a bubbling effect. The vat is also heated by resistors supplied with electricity so as to maintain a temperature of 80° to 100° C.

The oil is kept under these conditions for a period of 20 to 35 hours, depending on the origin of the lipids, especially for 25 hours in the case of the safflower oil considered in this Example, in order to obtain a degree of peroxidation according to the invention.

The oil thus obtained after peroxidation is stored in a storage tank receiving peroxidized safflower oil which may come from several peroxidation vats.

The peroxidized safflower oil obtained by the method indicated above has the following principal characteristics:

| peroxide number | 149.0 meq/kg |
|---|---|
| oxidized glyceride | 11.30% |
| viscosity at 50° C. | 25.9 centistokes |

This peroxidized oil can be used to prepare soft-walled capsules encapsulating the peroxidized safflower oil and releasing the peroxidized safflower oil on topical application by massage.

To do this, the peroxidized safflower oil can be encapsulated by any conventional methods of encapsulation in a soft capsule whose envelope is made mainly of a gelatin-water/glycerol mixture, the respective compositions of the content of the soft capsule and the envelope of the capsule being as follows for a batch of 635.415 kg, for example, making it possible to prepare 600,000 capsules in multiples and submultiples:

| A - Content of the soft capsules | |
|---|---|
| peroxidized safflower oil | 136.800 kg |
| aniseed fragrance | 3.00 kg |
| colloidal silica | 10.200 kg |
| | 150.000 kg |

| B - Envelope (wall of the soft capsules) | |
|---|---|
| gelatin | 211.796 kg |
| glycerol | 106.357 kg |
| purified water | 164.147 kg |
| titanium dioxide | 2.414 kg |
| | 485.415 kg |

The machine used makes it possible for example to prepare 460 mg soft capsules, which thus have the following composition:

| Content | mg/capsule |
|---|---|
| Peroxidized safflower oil | 228.000 mg |
| Aniseed fragrance ref. 9/500918 | 5.000 mg |
| Colloidal silica | 17.000 mg |
| For a content of | 250.000 mg |
| Envelope | 210.000 mg ± 10% |
| Titanium dioxide 0.75% | |
| Mixture of gelatin-water/glycerol (67/33) q.s. % | |
| For a capsule of | 460.000 mg ± 5% |

EXAMPLE 2

Measurement of the deep and peripheral circulation by rheoplethysmography a. Principle of the measurement The test is performed over an area of 10×10 cm on the calves (5 cm below the lower end of the knee-cap).

These zones are covered, by gentle massage, with a few drops of pure peroxidized safflower oil obtained in Example 1.

The measurements are made at T=0 (before application of the products) and T=5 min after application of the pharmaceutical composition, once on the right calf and once on the left calf.

Two electrodes for measuring volume variations are placed at the upper and lower ends.

A cuff is placed around the thigh. It is inflated to a pressure of 5 cm Hg so as to allow blood to enter the limb under examination while preventing the "venous return".

The volume variations are recorded in this limb segment. At the moment of occlusion, there is an increase up to a maximum value. This initial volume variation represents the increase in arterial flow.

When the maximum value is reached, the cuff is deflated. The venous drainage takes place with a curve of initially rapid and then slow decay. The angle corresponding to the ascending gradient of the filling curve is studied.

A comparable test is carried out in the absence of the composition.

b. Result

Comparison of the curves obtained after application of the peroxidized safflower oil according to the invention with the curves obtained in the absence of the composition made it possible to discern a significant increase in the arterial volumes in the first case, represented by an increase in the angle from 0.5 to 1.4 and from 0.4 to 1.5.

In other words, the peroxidized lipids used according to the invention cause an increase in blood flow of more than 100% on local application.

EXAMPLE 3

Continuous Doppler measurement of the circulation rates a. Principle of the measurement To perform this study, the subject is sitting down with his hands placed on a flat surface.

The radial, cubital, interosseous and pulpal arteries are studied by the Doppler method in the basal state T=0. The superficial veins are also examined.

Pure peroxidized safflower oil according to the invention, obtained in Example 1, is spread over the fingers of both the subject's hands. As it was impossible to study all ten fingers at once, the following were arbitrarily studied:

the flow in the distal phalanges (pulpal flow) of the right index finger and ring finger;
the flow in the left thumb (interosseous space).

A small amount of product was spread over each of these segments with gentle massage.

The subject does not move his hands during the 30 min of the examination.

The flows are recorded after 1 min, 5 min, 10 min and 30 min. Measurements are also made up to 6 h.

The results obtained showed a very marked increase in both the arterial and the venous flows (increase in the systolic-diastolic areas) as from the 1st minute, with maintenance beyond the 30th min. The curves also showed this maintenance up to 6 h.

No pain was observed in the skin of the fingers covered with the product. No redness was observed, which rules out a revulsive action of the product.

EXAMPLE 4

Analysis of the effect of the peroxidized lipids on subjects suffering from Raynaud's disease An attempt was made to demonstrate the activity of a composition based on peroxidized lipid on two female patients suffering from an attack of Raynaud's disease at the time of measurement.

The study was carried out on one hand.

The measurements were made by means of a Doppler apparatus.

The curves obtained with pure peroxidized safflower oil of Example 1 showed an increase in the vascularization with gradual reappearance of the Ressaut wave. At the same time, a very marked return of color to the fingers treated with this composition was observed between the 15th and the 45th min. This finding is consistent with the increase in the pulpal flow observed.

EXAMPLE 5

Analysis of the effect of a composition based on peroxidized lipids in the treatment of male sexual asthenia It is known that sexual asthenia is often associated with an arterial-venous problem.

Measurements of the variation in blood flow in the arterial and venous supply network of the corpus cavernosum penis were made before and after application of a capsule containing a 460 mg dose, obtained in Example 1; this is cut open to release the peroxidized safflower oil, which is spread with gentle massage.

The Doppler measurements made on the penis demonstrated a significant increase in the blood flows.

A clinical study on a significant number of subjects showed that the peroxidized lipids lead to conclusive results on sexual dysfunction after 45 d of treatment by local application.

The use of the peroxidized lipids according to the invention also makes it possible to hope for a notable improvement in complaints such as trophic disorders of the lower limbs, peripheral and arterial venous insufficiencies or diabetic arteriopathy.

What is claimed is:

1. A pharmaceutical composition for the treatment of circulatory insufficiencies in a mammal by local application wherein said composition contains a peroxidized lipid, having a degree of peroxidation of between 50 and 200 milliequivalents per kilogram.

2. A pharmaceutical composition according to claim 1 wherein the degree of peroxidation is comprised between 50 and 150 milliequivalents per kilogram.

3. A pharmaceutical composition according to claim 1 wherein the afore-mentioned peroxidized lipid is a peroxide obtained by the oxidation of lipids of vegetable origin.

4. A pharmaceutical composition according to claim 3 wherein the lipid of vegetable origin is in the form of at least one natural vegetable oil selected from the group consisting of sweet-almond oil, hazelnut oil, peanut oil, maize oil, grapeseed oil, sesame oil and safflower oil.

5. A pharmaceutical composition according to claim 1 wherein the afore-mentioned peroxidized lipid advantageously has a content of oxidized glycerides of between 5 and 40%.

6. A pharmaceutical composition according to claim 1 in the form of a cream, a gel, a liquid or soft capsules containing the peroxidized lipids.

7. A pharmaceutical composition according to claim 1 comprising between 2 and 99% by weight of peroxidized lipids.

8. A pharmaceutical composition according to claim 1 comprising furthermore about 1% of fragrance, as well as pharmaceutically acceptable excipients and demineralized water.

9. A method of use of peroxidized lipids, having a degree of peroxidation of between 50 and 200 milliequivalents per kilogram, preferably of between 50 and 150 milliequivalents per kilogram, for the preparation of a pharmaceutical composition intended for the treatment of circulatory insufficiencies, and in particular male sexual asthenia, by local application.

10. A method of use according to claim 9 wherein the afore-mentioned peroxidized lipid is a peroxide obtained by the peroxidation of lipids of vegetable origin, for example in the form of at least one natural vegetable oil.

11. A method of use according to claim 2 wherein the natural vegetable oil is selected from the group consisting of sweet-almond oil, hazelnut oil, peanut oil, maize oil, grapeseed oil, sesame oil and safflower oil.

12. A method of use according to claim 9 wherein the afore-mentioned peroxidized lipids advantageously have a content of oxidized glycerides of between 5 and 40%.

13. A method of use according to claim 9 wherein the pharmaceutical composition is prepared in the form of a cream, a gel, a liquid or soft capsules containing the peroxidized lipids.

14. A method of use according to claim 9 wherein the afore-mentioned pharmaceutical composition comprises between 2 and 99% by weight of peroxidized lipids.

15. A method of use according to claim 9 wherein the afore-mentioned pharmaceutical composition also comprises about 1% of fragrance, as well as pharmaceutically acceptable excipients and demineralized water.

16. A method for the treatment of circulatory insufficiencies in a mammal comprising the local application of a composition containing an effective amount of at least a peroxidized lipid, having a degree of peroxidation of between 50 and 200 milliequivalents per kilogram.

17. A method according to claim 16 for the treatment of male sexual asthenia.

18. A method according to claim 16 wherein the degree of peroxidation is comprised between 50 and 150 milliequivalents per kilogram.

19. A method according to claim 16 wherein the afore-mentioned peroxidized lipid is a peroxide obtained by the oxidation of lipids of vegetable origin.

20. A method according to claim 19 wherein the lipid of vegetable origin is in the form of at least one natural vegetable oil selected from the group consisting of sweet-almond oil, hazelnut oil, peanut oil, maize oil, grapeseed oil, sesame oil and safflower oil.

21. A method according to claim 16 wherein the afore-mentioned peroxidized lipid advantageously has a content of oxidized glycerides of between 5 and 40%.

22. A method according to claim 16 wherein the pharmaceutical composition is in the form of a cream, a gel, a liquid or soft capsules containing the peroxidized lipids.

23. A method according to claim 16 wherein the composition comprises between 2 and 99% by weight of peroxidized lipids.

24. A method according to claim 16 wherein the composition also comprises about 1% of fragrance, as well as pharmaceutically acceptable excipients and demineralized water.

25. A method for the treatment of circulatory insufficiencies associated with male sexual asthenia comprising the local application of a composition containing an effective amount of at least a peroxidized lipid, having a degree of peroxidation of between 50 and 200 milliequivalents per kilogram.

* * * * *